15
United States Patent
Gordon

(10) Patent No.: US 7,664,543 B2
(45) Date of Patent: Feb. 16, 2010

(54) CT SCANNER FOR AND METHOD OF IMAGING A PRESELECTED PORTION OF THE LOWER ABDOMEN REGION OF A PATIENT

(75) Inventor: Bernard M. Gordon, Manchester-by-the-Sea, MA (US)

(73) Assignee: Analogic Corporation, Peabody, MA (US)

(*) Notice: Subject to any disclaimer, the term of this patent is extended or adjusted under 35 U.S.C. 154(b) by 1434 days.

(21) Appl. No.: 10/133,054

(22) Filed: Apr. 26, 2002

(65) Prior Publication Data

US 2002/0196893 A1 Dec. 26, 2002

Related U.S. Application Data

(60) Provisional application No. 60/286,638, filed on Apr. 26, 2001, provisional application No. 60/316,514, filed on Aug. 31, 2001.

(51) Int. Cl.
*A61B 6/00* (2006.01)

(52) U.S. Cl. .................. 600/431; 600/407; 600/429; 600/427; 600/436; 378/15; 378/19; 378/62; 378/64; 606/130

(58) Field of Classification Search .................. 600/431, 600/426, 407, 427, 436, 429; 250/302; 606/130; 378/15, 19, 62, 64
See application file for complete search history.

(56) References Cited

U.S. PATENT DOCUMENTS 3,927,326 A * 12/1975 Kunne et al. ................ 378/179
4,503,331 A * 3/1985 Kovacs et al. ............ 250/363.04
4,547,893 A * 10/1985 Gordon ........................ 378/19
4,870,279 A * 9/1989 Cueman et al. .............. 250/368
4,961,208 A * 10/1990 Okada ......................... 378/18
5,109,397 A * 4/1992 Gordon et al. ............. 378/205

(Continued)

FOREIGN PATENT DOCUMENTS

WO WO 02/11771 A2 2/2002

OTHER PUBLICATIONS

Ralph Weissleder, et al., "Molecular Imaging", Molecular analysis Radiology and radiologists, Research Review, Radiology 2001, vol. 219 No. 2, pp. 316-333, 2001.

(Continued)

*Primary Examiner*—Brian Casler
*Assistant Examiner*—John F Ramirez
(74) *Attorney, Agent, or Firm*—McDermott Will & Emery, LLP

(57) ABSTRACT

A CT scanner and method are designed to scan a preselected portion of a patient's lower abdomen. The scanner may include a source and detector array designed to rotate about a rotation axis oriented substantially parallel to or coincident with the hips of the a patient so that a scanning plane does not pass through the patient's pelvic bones Higher-resolution image CT images can be achieved by using a detector array of the type used for digital radiography. The presence of prostatic cancer can be detected by first injecting the patient with a material including a high contrast material for X-ray imaging and a material for binding the high contrast material to a specific biological site if present in the preselected portion of the lower abdomen of the patient; and generating a CT image of the preselected portion of the lower abdomen.

50 Claims, 3 Drawing Sheets

U.S. PATENT DOCUMENTS

| | | | | |
|---|---|---|---|---|
| 5,114,703 | A | * | 5/1992 | Wolf et al. ................. 424/9.32 |
| 5,141,739 | A | * | 8/1992 | Jung et al. ................. 424/9.43 |
| 5,391,879 | A | * | 2/1995 | Tran et al. ................... 250/367 |
| 5,438,602 | A | | 8/1995 | Crawford |
| 5,468,465 | A | * | 11/1995 | Deutsch et al. .............. 424/9.4 |
| 5,574,763 | A | * | 11/1996 | Dehner ........................ 378/17 |
| 5,796,802 | A | * | 8/1998 | Gordon .......................... 378/8 |
| 5,848,117 | A | * | 12/1998 | Urchuk et al. ................ 378/19 |
| 6,017,703 | A | * | 1/2000 | Kinders et al. ................. 435/6 |
| 6,019,957 | A | * | 2/2000 | Miller et al. .............. 424/1.65 |
| 6,090,559 | A | | 7/2000 | Russell et al. |
| 6,136,311 | A | | 10/2000 | Bander |
| 6,171,796 | B1 | | 1/2001 | An et al. |
| 6,292,529 | B1 | | 9/2001 | Marcovici et al. |
| 6,366,796 | B1 | * | 4/2002 | Yanof et al. ................. 600/407 |
| 6,400,791 | B1 | * | 6/2002 | Schwarz ....................... 378/17 |
| 6,487,438 | B1 | * | 11/2002 | Widmark et al. ............ 600/431 |
| 6,735,274 | B1 | * | 5/2004 | Zahavi et al. ................. 378/15 |
| 7,167,538 | B2 | * | 1/2007 | Strobel et al. ................ 378/17 |
| 7,224,764 | B2 | * | 5/2007 | Sukovic et al. ................ 378/19 |

OTHER PUBLICATIONS

A.R. Bradwell, et al., "Developments in Antibody Imaging", Monoclonal Antibodies for Cancer Detection and Therapy, Chapter 4, pp. 65-85, 1985.

Judd W. Moul, et al., "The Role Of Imaging Studies And Molecular Markers For Selecting Candidates For Radical Prostatectomy", Urologic Clinics Of North America, Radical Prostatectomy, vol. 28, No. 3, pp. 459-472, Aug. 2001.

Alan W. Partin, et al., "The Clinical Usefulness Of Prostate Specific Antigen: Update 1994", The Journal Of Urology, vol. 152, 1358-1368, Nov. 1994.

Akhouri A Sinha, "Intravenous Injection of an Immunoconjugate (anti-PSA-IgG Conjugated to 5-Fluoro-2'-deoxyuridine) Selectively Inhibits Cell Proliferation and Induces Cell Death in Human Prostate Cancer Cell Tumors Grown in Nude Mice", Anticancer Research 19, pp. 893-902, 1999.

Catherine C. Boring, "Cancer Statistics, 1993", CA-Cancer J. Pract., vol. 43, No. 1, pp. 7-8, Jan./Feb. 1993.

G. Frens, "Controlled Nucleation For The Regulation Of The Particles Size In Monodisperse Gold Suspensions", Nature Physical Science, vol. 241, pp. 2-4, Jan. 1, 1973.

G. Dhom, "Epidemiologic Aspects of Latent and Clinically Manifest Carcinoma of the Prostate", Cancer Res. Clin. Oncol., 106:210-218, 1983.

H. Ballentine Carter, et al., "The Prostate: An Increasing Medical Problem", The Prostate 16:39-48, 1990.

Ganesh V. Raj, et al., "Clinical Utility of Indium 111-Capromab Pendetide Immunoscintigraphy in the Detection of Early, Recurrent Prostate Carcinoma after Radical Prostatectomy", Cancer, vol. 94, No. 4, pp. 987-996, Feb. 15, 2002.

Daniel Kahn, et al., "Radioimmunoscintigraphy With In-111-Labeled Capromab Pendetide Predicts Prostate Cancer Response to Salvage Radiotherapy After Failed Radical Prostatectomy", Journal of Clinical Oncology, vol. 16, No. 1, pp. 284-289, Jan. 1998.

S. Kirac, et al., "Detection of Metastatic Bone Lesions in Patients with Prostate Carcinoma: $^{99}Tc^m$-monoclonal antibody imaging", Nuclear Medicine Communications, vol. 18, pp. 968-973, 1997.

Daniel Kahn, et al., "$^{111}$Indium-Capromab Pendetide In The Evaluation Of Patients With Residual Or Recurrent Prostate Cancer After Radical Prostatectomy", The Journal Of Urology, vol. 159, pp. 2041-2047, Jun. 1998.

Akhouri A. Sinha, et al., "Plasma Membrane Association of Cathepsin B in Human Prostate Cancer: Biochemical and Immunogold Electron Microscopic Analysis", The Prostate 49: 172-184, 2001.

Harriet M. Lamb, et al., "Capromab Pendetide-A Review of its Use as an Imaging Agent in Prostate Cancer", Drugs & Aging, Apr. 12, 1998 (4) 293-304.

Rodney J. Ellis, et al., "Radioimmunoguided Imaging Of Prostate Cancer Foci With Histopathological Correlation", Int. J. Radiation Oncology Biol. Phys., vol. 49, No. 5, pp. 1281-1286, 2001.

G.P. Murphy, et al., "The National Survey Of Prostate Cancer In The United States By The American College Of Surgeons", The Journal Of Urology, vol. 127, pp. 928-934, May 1982.

Timo Phronen, et al., "Immunofluorometric Assay For Sensitive And Specific Measurement Of Human Prostatic Glandular Kallikrein (hK2) In Serum", Clinical Chemistry 42:7, 1034-1041, 1996.

Julius S. Horoszewicz, et al., Monoclonal Antibodies to a New Antigenic Marker in Epithelial Prostatic Cells and Serum of Prostatic Cancer Patients, Anticancer Research 7:927-936, 1987.

Thomas C. Gasser, et al., "MRI And Ultrasonography In Staging Prostate Cancer", The New England Journal Of Medicine, pp. 494-495, Feb. 14, 1991.

David A. Silver, et al., "Prostate-specific Membrane Antigen Expression in Normal and Malignant Human Tissues", Clinical Cancer Research, vol. 3, pp. 81-85, Jan. 1997.

Ron S. Israeli, et al., "Expression of the Prostate-Specific Membrane Antigen", Cancer Research, vol. 54, pp. 1807-1811, Apr. 1, 1994.

Matthew D. Rifkin, et al., "Comparison of Magnetic Resonance Imaging and Ultrasonography in Staging Early Prostate Cancer", The New England Journal of Medicine, Val. 323, No. 10, pp. 623-626, Sep. 6, 1990.

Gerald P. Murphy, et al., "Evaluation and Comparison of Two New Prostate Carcinoma Markers", Cancer, vol. 78, No. 4, pp. 809-818, Aug. 15, 1996.

Ruth E. Carter, et al., "Prostate-Specific Membrane Antigen is a Hydrolase with Substrate and Pharmacologic Characteristics of a Neuropeptidase", Neurobiology, Proc. Natl. Acad. Sci. USA, vol. 93, pp. 749-753, Jan. 1996.

G.P. Murphy, et al., "Comparison of Prostate Specific Antigen, Prostate Specific Membrane Antigen, and LNCaP-Based Enzyme-Linked Immunosorbent Assays in Prostatic Cancer Patients and Patients With Benign Prostatic Enlargement", The Prostate 26:164-168, 1995.

Chia-Ling Huang, et al., "Comparison of Prostate Secretory Protein With Prostate Specific Antigen and Prostatic Acid Phosphatase as a Serum Biomarker for Diagnosis and Monitoring Patients With Prostate Carcinoma", The Prostate 23: 201-212, 1993.

Catherine C. Boring, et al., "Cancer Statistics, 1993", CA Cancer J Clin., 43: 7-26, 1993.

Phyllis A. Wingo, et al., "An Adjustment to the 1997 Estimate for New Prostate Cancer Cases", CA Cancer J Clin. 47: 239-242, 1997.

\* cited by examiner

CT SCANNER FOR AND METHOD OF IMAGING A PRESELECTED PORTION OF THE LOWER ABDOMEN REGION OF A PATIENT

RELATED APPLICATIONS

This application claims priority from provisional applications U.S. Ser. Nos. 60/286,638, filed Apr. 26, 2001 and 60/316,514 filed Aug. 31, 2001.

BACKGROUND

The invention relates generally to non-invasively imaging a preselect portion of the lower abdomen and groin area of a patient with X-rays, at relatively lower radiation dosages than currently used in, and improved resolution than currently achievable with, conventional Computed Tomography (CT) scanning.

Various physiological changes can occur in the lower abdomen region of a patient requiring diagnostic and imaging approaches to aid medical personnel in diagnosing, prognosticating, and managing or otherwise treating these changes.

For example, as described in U.S. Pat. No. 6,171,796 (An, et al.) entitled Biomarkers and Targets for Diagnosis Prognosis and Management of Prostate Disease, carcinoma of the prostate (PCA) is the second-most frequent cause of cancer related death in men in the United States (citing Boring et al., CA-Cancer J. Pract., 43:7-26, 1993; and Wingo et. al., CA Cancer J. Clin., 47(4):239-242, 1997). The increased incidence of prostate cancer during the 1980s has established prostate cancer as the most prevalent of all cancers (citing Carter and Coffey, Prostate, 16:39-48, 1990). Although prostate cancer is the most common cancer found in United States men, (approximately 210,000 newly diagnosed cases/year), the molecular changes underlying its genesis and progression remain poorly understood (citing Boring et al., CA-Cancer J. Pract., 43:7-26, 1993). According to American Cancer Society estimates, the number of deaths from PCA is increasing in excess of 8% annually.

An unusual challenge presented by prostate cancer is that most prostate tumors do not represent life threatening conditions. Evidence from autopsies indicate that an estimated 11 million American men have prostate cancer (citing Dbom, Cancer Res. Clin. Oncol., 106:210-218, 1983). These figures are consistent with prostate carcinoma having a protracted natural history in which relatively few tumors progress to clinical significance during the lifetime of the patient. If the cancer is well-differentiated, organ-confined and focal when detected, treatment does not extend the life expectancy of older patients.

Unfortunately, the relatively few prostate carcinomas that are progressive in nature are likely to have already metastasized by the time of clinical detection. Survival rates for individuals with metastatic prostate cancer are quite low. Between these two extremes are patients with prostate tumors that will metastasize but have not yet done so. For these patients, surgical removal of their prostates is curative and extends their life expectancy. Therefore, early detection and determination of which group a newly diagnosed patient falls within is critical in determining optimal treatment and patient survival.

The most commonly utilized current tests for prostate cancer are digital rectal examination (DRE) and analysis of serum prostate specific antigen (PSA). Although PSA has been widely used as a clinical marker of prostate cancer since 1988 (citing Partin and Oesterling, J. Urol., 152:1358-1368, 1994), screening programs utilizing PSA alone or in combination with digital rectal examination have not been successful in improving the survival rate for men with prostate cancer (citing Partin and Oesterling, J. Urol., 152:1358-1368, 1994). While PSA is specific to prostate tissue, it is produced by normal and benign as well as malignant prostatic epithelium, resulting in a high false-positive rate for prostate cancer detection (citing Partin and Oesterling, J. Urol., 152:1358-1368, 1994).

Other markers that have been used for prostate cancer detection include prostatic acid phosphatase (PAP) and prostate secreted protein (PSP). PAP is secreted by prostate cells under hormonal control (citing Partin and Oesterling, J. Urol., 152:1358-1368, 1994). It has less specificity and sensitivity than does PSA. As a result, it is used much less now, although PAP may still have some applications for monitoring metastatic patients that have failed primary treatments. In general, PSP is a more sensitive biomarker than PAP, but is not as sensitive as PSA (citing Huang et al., Prostate, 23: 201-212, 1993). Like PSA, PSP levels are frequently elevated in patients with benign prostatic hypertrophy or hyperplasia (BPH) as well as those with prostate cancer.

Another serum marker associated with prostate disease is prostate specific membrane antigen (PSMA) (citing Horoszewicz et al., Anticancer Res., 7:927-936, 1987; Carter et al., Proc. Nat'l Acad. Sci. USA 93: 749-753, 1996; and Murphy et al., Cancer, 78: 809-818, 1996). PSMA is a Type II cell membrane protein and has been identified as Folic Acid Hydrolase (FAH) (Carter et al., Proc. Nat'l Acad. Sci. USA 93: 749-753, 1996). Antibodies against PSMA react with both normal prostate tissue and prostate cancer tissue (citing Horoszewicz et al., Anticancer Res., 7:927-936, 1987). In the cited Murphy et al. publication (Prostate, 26:164-168, 1995) Murphy et al. used ELISA to detect serum PSMA in advanced prostate cancer. As a serum test, PSMA levels are a relatively poor indicator of prostate cancer. However, PSMA may have utility in certain circumstances. PSMA is expressed in metastatic prostate tumor capillary beds (citing Silver et al., Clin. Cancer Res., 3: 81-85, 1997) and is reported to be more abundant in the blood of metastatic cancer patients (citing Murphy et al., Cancer, 78: 809-818, 1996). PSMA messenger RNA (mRNA) is down-regulated 8-10 fold in the LNCAP prostate cancer cell line after exposure to 5-.alpha.-dihydroxytestosterone (DHT) (citing Israeli et al., Cancer Research, 54:1807-1811, 1994).

A relatively new potential biomarker for prostate cancer is human kallekrein 2 (HK2) (citing Piironen et al., Clin. Chem. 42: 1034-1041, 1996). HK2 is a member of the kallekrein family that is secreted by the prostate gland. In theory, serum concentrations of HK2 may be of utility in prostate cancer detection or diagnosis, but the usefulness of this marker is still being evaluated.

U.S. Pat. Nos. 6,171,796 (An, et al.) and 6,090,559 (Russell, et al.) describe other biomarkers and targets for diagnosis prognosis and management of prostate disease.

As described in U.S. Pat. No. 6,136,311 (Bander), at the time of clinical diagnosis, as many as 25% of patients have bone metastasis demonstrable by radionuclide scans. Murphy, G. P., et al., "The National Survey Of Prostate Cancer In The United States By The American College Of Surgeons," J. Urol., 127:928-939 (1982). Accurate clinical evaluation of nodal involvement has proven to be difficult. Currently available imaging techniques such as computed tomography ("CT") or magnetic resonance imaging ("MRI") are unable to distinguish metastatic prostate cancer involvement of lymph nodes by criterion other than size. More specifically, current conventional, high resolution, CT scanners provide pixelated images limited to about 15 to 20 line pairs/cm, corresponding to imaged areas of about 500 to 1000 microns/pixel. Therefore, by definition, to date these imaging modalities are inherently insensitive in the detection of small volume (<500-1000 microns) disease as well as non-specific in the detection of larger volume adenopathy. A recent study assessed the accuracy of MRI in patients with clinically localized prostate cancer. Rifkin et al., "Comparison Of Magnetic Resonance Imaging And Ultrasonography In Staging Early Prostate Cancer," N. Engel. J. Med., 323:621-626 (1990). In this study, 194 patients underwent a MRI and 185 of these patients had a lymph node dissection. 23 (13%) patients had pathologically involved lymph nodes. MRI was suspicious in only 1 of these 23 cases resulting in a sensitivity of 4%. Similar results have also been noted with conventional CT scans. Gasser et al., "MRI And Ultrasonography In Staging Prostate Cancer," N. Engl. J. Med. (Correspondence), 324(7):49-495 (1991).

While resolution is a key drawback with current imaging techniques, current CT scanners require a gantry supporting the x-ray source and detectors to rotate around the patient, and in particular his hips and pelvic bones, requiring radiation at levels sufficient to transmit through dense bone in order to acquire adequate information to image the prostate and its soft tissue environs.

One diagnostic tool that has proved helpful in the detection of diseased tissue in the body is referred to as in vivo imaging. The term "in vivo imaging" refers to any method which permits the detection or measurement of a biological process using an imaging modality. It is usually accomplished in connection with cancer cells by using a biological agent administered to a patient, the agent being of the type that is localized to the tumor bearing the antigen with which the biological agent reacts, and is detected or "imaged" using an appropriate imaging modality. The prior art in vivo imaging modalities include known techniques such as radionuclear scanning using e.g., a gamma camera or emission tomography. See e.g., A. R. Bradwell et al., "Developments in Antibody Imaging", Monoclonal Antibodies for Cancer Detection and Therapy, R. W. Baldwin et al., (eds.), pp. 65-85 (Academic Press 1985), which is hereby incorporated by reference. Alternatively, a positron emission transaxial tomography (PET) scanner has been used where the radiolabel is a constrast agent that emits positrons. A more general discussion of molecular imaging is described in Weissleder, et al., "Molecular Imaging", Radiology, (Vol. 219, No. 2), May 2001, pp 316-333.

SUMMARY OF THE INVENTION

In accordance with one aspect of the invention a method of in vivo imaging of a preselected portion of the lower abdomen of a patient, comprises:
  injecting the patient with a material including a high contrast material for X-ray imaging and a material for binding the high contrast material to a specific biological site if present in the preselected portion of lower abdomen of the patient; and
  generating a CT image of the preselected portion of the lower abdomen of the patient so as to generate an image of the preselected portion of the lower abdomen of the patient and any of said high contrast material present therein.

In one embodiment, the high contrast material is a dense high Z element.

In one embodiment the high contrast material is a metal selected from the group consisting of gold and tungsten.

In one embodiment the material for binding the high contrast material to a specific biological site includes a molecular probe that binds with prostate or prostate carcinoma-specific markers.

In one embodiment the material for binding the high contrast material to a specific biological site includes a monoclonal antibody.

In one embodiment a CT image of the preselected portion of the lower abdomen includes generating a "non-plevic CT scanned image", wherein the CT image of the preselected portion of the lower abdomen is created without the necessity of X-rays passing through the pelvic bones of the patient. In this regard, the scanning plane for the CT image extends between, but does not extend through the pelvic bones of the patient.

In accordance with another aspect of the invention a CT scanner for in vivo imaging of a patient injected with a material including a high contrast material for X-ray imaging and a material for binding the high contrast material to a specific biological site if present in the lower abdomen of the patient, the scanner comprises:
  an X-ray source;
  a detector array including at least one row of detectors;
  a source and detector array support constructed and arranged so as to rotate the source and detector array about an rotation axis so as to define at least one scanning plane;
  a patient support constructed and arranged so as to support the patient in a specific orientation so that the scanning plane does not include the pelvic bones of the patient positioned on the patient support.

In one embodiment the high contrast material is a dense high Z element.

In one embodiment the high contrast material is a metal selected from the group consisting of gold and tungsten.

In one embodiment the material for binding the high contrast material to a specific biological site includes a molecular probe that binds with prostate or prostate carcinoma-specific markers.

In one embodiment the material for binding the high contrast material to a specific biological site includes a monoclonal antibody.

In one embodiment the source and detector array support rotates through a predetermined angle sufficient to acquire sufficient data for half scan reconstruction.

In one embodiment the source and detector are arranged so as to define a fan beam and fan beam angle, and the detector array rotates a minimum of approximately 180° plus an angle equal to the fan beam angle during a scan.

In one embodiment the patient support remains fixed as the source and detector array support rotates through said predetermined angle.

In one embodiment the patient support rotates from a preselected angle as the source and detector array support rotate through said predetermined angle.

In one embodiment the detector array is asymmetrical. In one embodiment the source and detector array support rotates through a predetermined angle sufficient to acquire sufficient data for half scan reconstruction.

In one embodiment the source and detector are arranged so as to define a fan beam and fan beam angle, and the detector array rotates a minimum of approximately 180° plus an angle equal to the fan beam angle during a scan.

In one embodiment the detector array is symmetrical.

In one embodiment the scanner is constructed and arranged so as to perform a constant z-axis position scan.

In accordance with yet another aspect of the invention, a CT scanner is provided for in vivo imaging a preselected portion of the lower abdomen of a patient injected with a material including a high contrast material for X-ray imaging and a material for binding the high contrast material to a specific biological site if present in the preselected portion of the lower abdomen of the patient so as to provide a high resolution image, the scanner comprising:

a detector array comprising a plurality of detectors, each having a maximum width dimension of 150 microns and a maximum length dimension of 150 microns.

In accordance with one embodiment the high contrast material is a dense high Z element.

In accordance with one embodiment the high contrast material is a metal selected from the group consisting of gold and tungsten.

In accordance with one embodiment the material for binding the high contrast material to a specific biological site includes a molecular probe that binds with prostate or prostate carcinoma-specific markers.

In accordance with one embodiment the material for binding the high contrast material to a specific biological site includes a monoclonal antibody.

In accordance with one embodiment the detectors are square.

In accordance with one embodiment each has a dimension on the order of 85 square microns.

In accordance with one embodiment the detectors are rectangular.

In accordance with another aspect of the invention a CT scanner is provided for in vivo imaging a preselected portion of the lower abdomen of a patient injected with a material including a high contrast material for X-ray imaging and a material for binding the high contrast material to a specific biological site if present in the lower abdomen of the patient so as to provide a high resolution image. The scanner comprises:

a detector array comprising a plurality of detectors, each having a maximum width dimension of 150 microns and a maximum length dimension of 150 microns.

In one embodiment the high contrast material is a dense high Z element.

In one embodiment the high contrast material is a metal selected from the group consisting of gold and tungsten.

In one embodiment the material for binding the high contrast material to a specific biological site includes a molecular probe that binds with prostate or prostate carcinoma-specific markers.

In one embodiment the material for binding the high contrast material to a specific biological site includes a monoclonal antibody.

In one embodiment the detectors are square. In another embodiment the detectors are rectangular.

In one embodiment, each detector has a dimension on the order of 85 square microns.

In accordance with another aspect of the invention, a method of scanning a preselected portion of the lower abdomen of a patient using computed tomography techniques comprises:

injecting the patient with a material including a high contrast material for X-ray imaging and a material for binding the high contrast material to a specific biological site if present in the lower abdomen of the patient; and positioning the patient within a CT scanner so that one or more scanning planes created by the rotation of the X-ray source and detector array of the scanner is provided between the pelvic bones of the patient.

In one embodiment the high contrast material is a dense high Z element.

In one embodiment the high contrast material is a metal selected from the group consisting of gold and tungsten.

In one embodiment the material for binding the high contrast material to a specific biological site includes a molecular probe that binds with prostate or prostate carcinoma-specific markers.

In one embodiment the material for binding the high contrast material to a specific biological site includes a monoclonal antibody.

In one embodiment the method further includes rotating the source and detector array through a predetermined angle sufficient to acquire sufficient data for half scan reconstruction.

In one embodiment the source and detector are arranged so as to define a fan beam and fan beam angle, and including rotating the detector array a minimum of approximately 180° plus an angle equal to the fan beam angle during a scan.

In one embodiment the patient is fixed as the source and detector array rotate through the predetermined angle.

In one embodiment the method further comprises: rotating the patient support through a preselected angle as the source and detector array support rotate through said predetermined angle.

In one embodiment the method further includes using a asymmetrical detector array.

In one embodiment the method further comprises rotating the source and detector array through a predetermined angle sufficient to acquire sufficient data for half scan reconstruction.

In one embodiment the method includes arranging the source and detector so as to define a fan beam and fan beam angle, and rotating the detector array at least 180° plus an angle equal to the fan beam angle during a scan.

In one embodiment the method comprises using a symmetrical detector array.

In one embodiment the method comprises performing a constant z-axis position scan.

In one embodiment the method comprises:

using a detector array comprising a plurality of detectors, each having a maximum width dimension of 150 microns and a maximum length dimension of 150 microns so as to increase the resolution of an image generated from data acquired by the scanner.

In one embodiment the method comprises using a detector array comprising a plurality of square detectors.

In one embodiment the method comprises using a detector array comprising detectors, each on the order of 85 square microns.

In one embodiment the method comprises using a detector array comprising a plurality of rectangular detectors.

In accordance with another aspect of the invention, a method of providing a high resolution image of a preselected portion of the lower abdomen of a patient injected with a material including a high contrast material for X-ray imaging and a material for binding the high contrast material to a specific biological site if present in the preselected portion of the lower abdomen of the patient, comprises:

forming the image using a detector array comprising a plurality of detectors, each having a maximum width dimension of 150 microns and a maximum length dimension of 150 microns.

In one embodiment the high contrast material is a dense high Z element.

In one embodiment the high contrast material is a metal selected from the group consisting of gold and tungsten.

In one embodiment the material for binding the high contrast material to a specific biological site includes a molecular probe that binds with prostate or prostate carcinoma-specific markers.

In one embodiment the material for binding the high contrast material to a specific biological site includes a monoclonal antibody.

In one embodiment the detectors are square.

In one embodiment the detectors are 85 microns square.

GENERAL DESCRIPTION OF THE DRAWINGS

DETAILED DESCRIPTION OF THE DRAWINGS

The invention relates to an imaging system that provides reconstructed images having better resolution than images provided by conventional CT scans, and at relatively reduced radiation levels.

The system is designed with a suitable support for supporting an X-ray source and a detector array at diametrically opposite sides of, and rotatable about a substantially horizontal rotation axis. When a patient lying on a patient pallet or table is properly positioned relative to the system, the rotation axis extends substantially horizontally through or substantially parallel to the hips of the patient so that the X-ray source and detector array can rotate between the legs of the patient. This enables the X-ray source and detector array to be positioned more closely to the patient during a scan so as to reduce the required X-ray emission for the scan, and image an area of the lower abdomen, such as portions of the prostate, without the necessity of transmitting X-rays through a significant portion of the pelvic bones of the patient. In addition, detector arrays are available to provide significantly higher resolution than currently available with conventional CT scanners.

Figure 1:
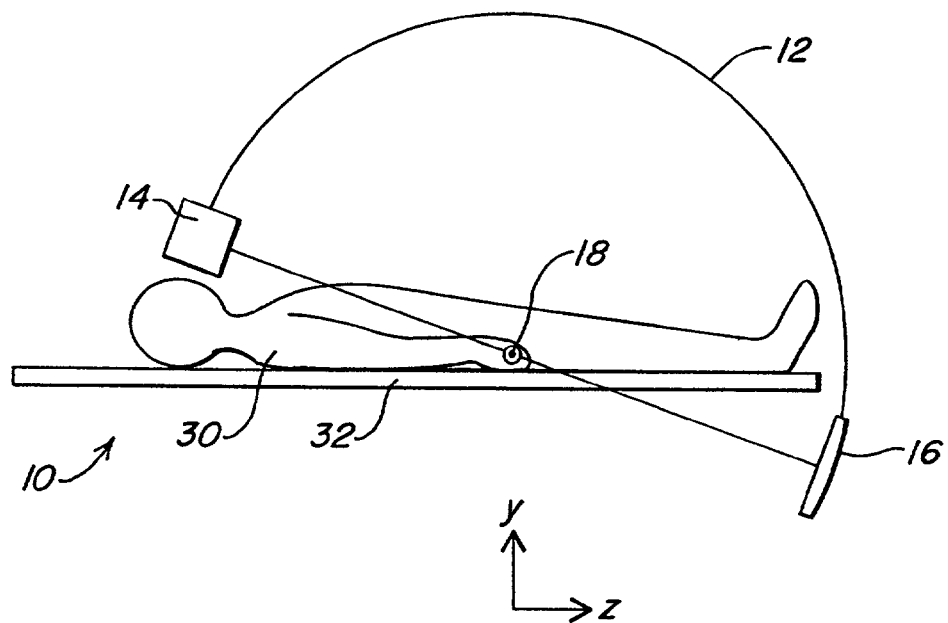
FIG. 1 illustrates a side view of a scanning system constructed in accordance with the present invention.
Figure 2:
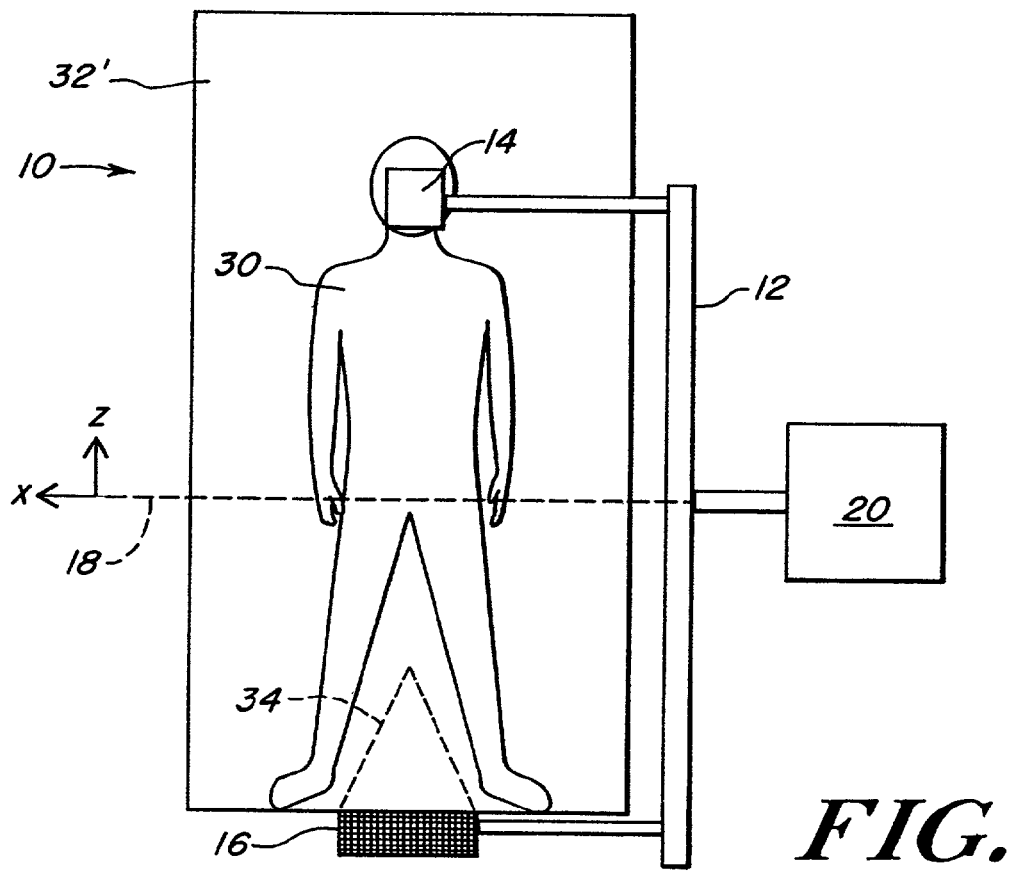
FIG. 2 illustrates a top view of the scanning system of FIG. 1.

One embodiment of the imaging system is shown at 10 in FIGS. 1 and 2. As shown in these figures, the system includes a support 12, preferably in the form of a C-arm, although other support structures can be used. The support 12 supports a source 14 of X-rays and a detector array 16. The support 12 is suitably constructed and arranged so that it can rotate about the rotation axis 18, at least through a limited predetermined angle.

As seen in FIG. 2, the support 12 is suitably coupled to a driving mechanism 20, including a motor, for rotating the support about the rotation axis 18 during a scan through a predetermined number of successive rotation angles from a starting position to a final position, described more fully hereinafter, and counter rotate the support 12 about the axis following a scan to reposition the support at the starting position.

Figure 3:
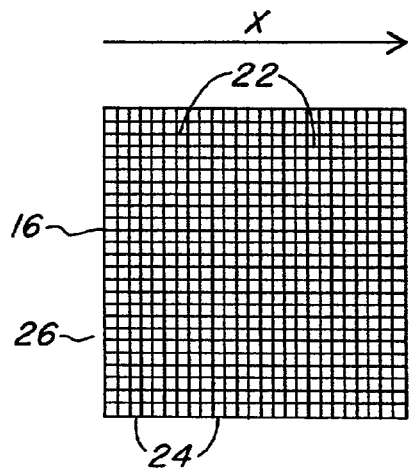
FIG. 3 illustrates a frontal view showing the relationship of a source and detector array of a CT scanning system.
Figure 4:
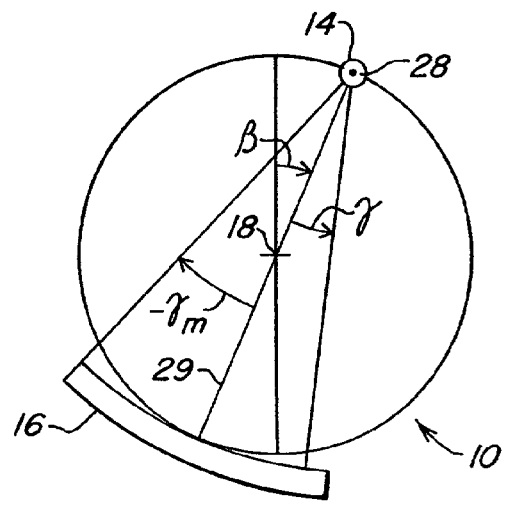
FIG. 4 illustrates a frontal view showing the relationship of a source and asymmetric detector array of a CT scanning system.
Figure 5:
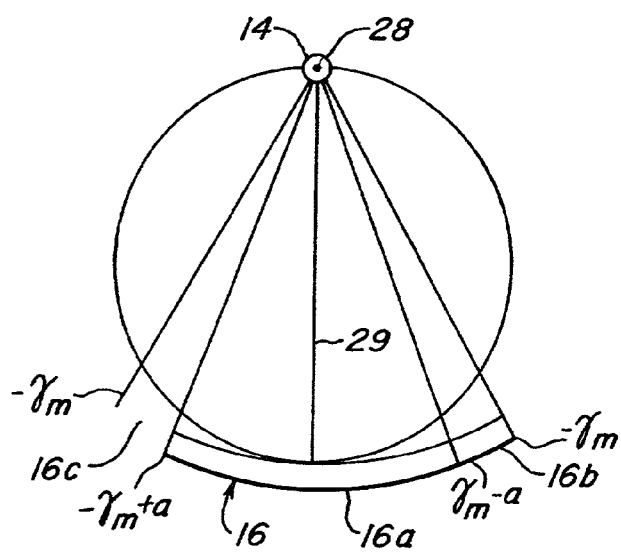
FIG. 5 illustrates a generalized block diagram showing basic elements of an architecture from processing the data signals generated by the detectors of the detector array.

As shown in FIG. 3, the detector array 16 includes individual detector elements 22 disposed in either a single row, or preferably multiple rows and columns, with each row 24 rotating about the axis 18, while each column 26 remains parallel to the axis 18, during a scan. The array can be flat or curved. If curved, the array preferably, as shown in FIG. 4, is constructed in the form of an arc of a circle having a center of curvature at the point 28, referred to as the "focal spot", where the radiation emanates form the X-ray source 14. The X-ray source 14 and each row 24 of detector elements are preferably positioned so that the X-ray paths between the source and the detector elements of each row all lie in a "scanning plane" that is normal to, or substantially normal to the rotation axis 18. The X-rays originate from what is substantially a point source and extend at different angles to the detector elements 22 of a row 24 all within the same plane, with the X-rays extending from the focal spot to each detector element being referred to as a ray. The rays form a "fan beam" with each row of detector elements 22. The detector elements 22 can be arranged so as to be symmetrical or asymmetrical about a bisecting ray 29 of the fan beam passing from the focal spot through the axis 18 to the detector array, as illustrated in FIGS. 4 and 5, respectfully.

As will be more apparent hereinafter, during a scan, as best shown in FIG. 4, the source 14 and detector array 16 rotate about the axis 18, partially around the patient 30 (shown in proper position in FIG. 2) being scanned, allowing the scanner 10 to generate a set of projections $P_j(\beta, \gamma)$ at a corresponding set of projection angles $\beta$. The rotation can be a smooth and continuous movement, or it can be in discrete steps stopping at each projection angle $\beta$ in order to acquire data for the view at each angle (a so-called "step and shoot" approach). Since the patient being imaged by the system 10 remains at a constant X-axis position during the scan, conventional scanning techniques used by a conventional CT scanner can be used with the system 10, wherein the patient remains at a constant Z-axis position, and so called "Constant Z-axis position scanning" or CZA scanning can be performed.

Using well known algorithms, such as the inverse Radon transform, a tomogram may be generated from a set of projections that all share the same scanning plane, and this common scanning plane as mentioned above is referred to as the "slice plane". In this case multiple slice planes are defined by the corresponding rows 24 of the detector array 16. A tomogram is representative of the density of a two dimensional "slice" along the slice plane of the object being scanned. The process of generating a tomogram from the projections is commonly referred to as "filtered back projection" or "reconstruction", since the tomogram may be thought of as being reconstructed from the projection data. Accordingly, the system 10 would include a back projector as a part of a reconstruction computer, described below in connection with FIG. 6, for each row of detector elements generating the tomograms from the projections.

The source 12 can be a conventional source of X-rays of the type currently used in CT scanners, although it can be operated at a lower power level since the source can be placed closer to the mechanical rotation center of the machine, corresponding to the "isocenter" of a reconstructed image, than the corresponding spacing provided in conventional CT scanner systems.

The detector array 16 is preferably a two dimensional array of multiple rows and columns of detector elements. The detector array can, however, include of any number of rows and columns, use any materials or constructed that are known for use as detectors. Preferably, the detector elements are as small as possible, i.e., on the order of about 150 microns in length or less, and on the order of about 150 microns in width or less. The individual detectors can be of any geometric shape that provides the desired array motif, with square and rectangular shapes being preferred, and could be staggered if the design required such an arrangement. In one embodiment, a commercially available plate used for digital radiography can be used to provide relatively small sized detectors. A current state of the art 1000×1000 (10 cm×10 cm) detector array plate designed for digital radiography includes detector elements on the order of 85 microns square. An example of the construction and materials for such an array are shown and described in U.S. Pat. No. 6,292,529, entitled "Two-dimensional X-ray Detector Array for CT Applications", issued in the name of Marcovici et al on Sep. 18, 2001 and assigned to present assignee (the disclosure of which is incorporated by reference), except that the detectors 22 of the scanner 10 are substantially reduced in size, similar to those provided in the arrays used for digital radiography. It should be appreciated that other detector arrangements can be utilized depending on the particular design requirements.

As shown in FIG. 3 each of the rows 24 of the detector array 16 is defined as each set of aligned detector elements 22 which rotate about the X-axis, even though during a scan they move in substantially parallel planes oriented in substantially the vertical direction. These parallel planes define the scanning planes. The columns 26 are each defined as a set of aligned detector elements, which remain parallel to the X-axis during a scan.

As will be appreciated below, the rotation axis 18 intersects the scanning planes at the mechanical center of rotation, which corresponds to the isocenter of each reconstructed image provided by a corresponding row 24 of detectors. Each rotating row 24 thus can provide a single slice through the field of view defined by the area prescribed by rotating source and row. By using multiple rows one obtains multiple image slices corresponding to the number of rows so that an image of each slice can be generated. Techniques are known for using the data from multiple slice planes to provide a volumetric image. As best seen in FIG. 1, the rotation axis 18 passes through or is substantially parallel to the hips of the patient 30. Using a conventional CT scanner reference system, where an X-ray source and detector array rotate on a gantry about the Z-axis of the scanner, the rotation axis 18 of the support 12 of the embodiment of FIGS. 1 and 2 corresponds to a horizontal X-axis of a conventional scanner reference system (the X, Y and Z axes of a conventional CT system are shown in FIGS. 1 and 2), which in this case is normal to the Z-axis, and remains horizontal, or nearly horizontal during a scan by the imaging system.

CT scanning techniques can be employed to acquire imaging data from the amount of x-ray photons acquired by each detector 22 during each of a plurality of projection views at predefined projection angles as the source and detector array rotate about the rotation axis 18. For example, half scan reconstruction requires that the source and the detector row 24 rotate only 180° plus an angle equal to the fan beam angle (the angle of the X-ray fan beam that extends from the focal spot to the outer edges of the row of detectors).

Figure 6:
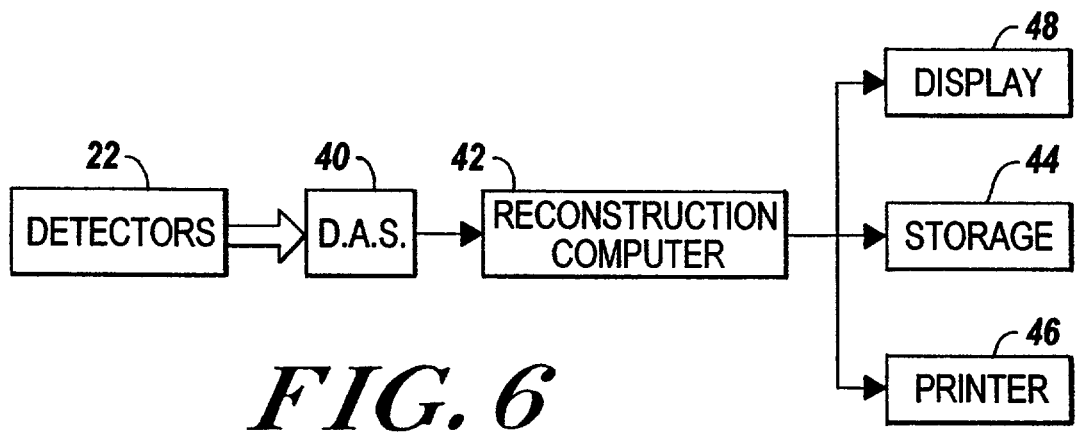
FIG. 6 illustrates a side view of an alternative scanning system constructed in accordance with the present invention.

In order to process the data, as shown in FIG. 6, the detectors 22 of the array 16 are coupled to a data acquisition system (DAS) 40 which acquires the data representing the amount of x-rays absorbed along each ray path for each projection from the focal spot 28 to each detector 22. The data is transferred from the DAS 40 to a reconstruction computer 42, the latter including a back projector, for generating the image data represented by the scan. The image data can be transferred to archival storage 44, a printer 46, and/or a display 48, either directly, or through a local area network, or wide area network such as the internet.

In preparation of a scan, as best seen in FIG. 2, a patient 30 can be positioned on a patient pallet or table 32 specifically designed to be used with the imaging system 10. In the proper position, the source 14 and detector array 16 are disposed between and capable of being rotated about an arc that circumscribes portions of the lower abdomen of the patient without the necessity of X-rays passing through the pelvic bones. Because of the closer spacing and the reduced amount of bone that must be traversed by the X-ray photons, the overall power requirements of the system are reduced. The spacing between the patient and the X-ray source can be further reduced (further reducing the power requirements) by, for example, creating a space (shown by dotted line 34 in FIG. 2) in the table 32 so that the source 14 and/or the detector array 16 can move within that space. In this way the spacing is not limited by the edge of the table 32.

As in CZA scanning, all the projections corresponding to a row of detector elements share a common scanning plane, so these projections may be applied directly to the back projector for generation of a tomogram.

Tomograms created from data acquired from conventional CT scanners (where the source and detectors mounted on a gantry can continuously rotate about the Z-axis) may be reconstructed from a set of fan beam projections $P_f(\beta, \gamma)$ where $\beta$ is the projection angle and is in the range $(0, \beta_{max})$, and $\gamma$ is the detector angle measured by the angle of a ray passing from the focal spot to the detector and a bisector ray bisecting the fan beam. The choice of $\beta_{max}$ depends in part of the desired signal-to-noise ratio of the tomogram and in part on the desired slice plane width of the tomogram. Due to the rotational nature of CT scanners, the ray used to measure the data point $P_f(\beta, \gamma)$ is coincident with the ray used to measure the data point $P_f(\beta+2\pi, \gamma)$. So, in the absence of patient motion in a direction parallel to the rotation (Z-) axis, projection data is periodic with period $2\pi$, and the data point $P_f(\beta, \gamma)$ equals the data point $P_f(\beta+2\pi, \gamma)$. One method of generating a tomogram from CZA scan data uses $\beta_{max}$ equal to $2\pi$. Since the gantry rotates completely around the patient, this type of scanning is often referred to as "fullscan". It is unnecessary to set $\beta_{max}$ greater than $2\pi$ since due to the periodicity of the projection data, this will result in collecting redundant data.

In addition to the above-described fullscan periodicity or redundancy, CT scanners also have an associated "halfscan" redundancy that is described by the following Equation (1).

$$P_f(\beta, \gamma) = P_f(\beta+\pi-2\gamma, -\gamma) \tag{1}$$

Equation (1) is true in the absence of patient motion because the ray used to measure the data point $P_f(\beta, \gamma)$ is coincident and antiparallel to the ray used to measure the data point $P_f(\beta+\pi-2\gamma, -\gamma)$. The rays are "antiparallel" because the relative positions of the X-ray source and detector are reversed. Known CT "halfscan" techniques use Equation (1) to permit generation of a tomogram from a set of CZA fan beam projections collected with $\beta_{max}$ equal to $\pi+2\gamma_m$. However, such a half scan tomogram will have a lower signal-to-noise ratio than a fullscan tomogram where $\beta_{max}$ equals $2\pi$.

An improved half scan technique is described in U.S. Pat. No. 5,848,117 issued in the name of Urchuk et al., assigned to the present assignee. This technique requires an asymmetric detector arrangement where the bisector array extending from the focal spot through the center of the beam does not intersect the detector array in the center of each row, but some angular spacing therefrom. This detector system includes a symmetric portion extending from detector angle $-\gamma_m+\alpha$. to $+\gamma_{m-}\alpha$, and an asymmetric portion 16b extending from detector angle $+\gamma_{m-}\alpha$ to $+\gamma_m$, where $\alpha$ is the angular extent of the asymmetric portion ($\alpha>0$). Detector array 16 may also be thought of as not including a portion 16c extending from detector angle $-\gamma_m$ to $-\gamma_m+\alpha$. If detector array 16 did include the missing portion 16c, then the detector system would be symmetric. A fan beam projection generated by asymmetric detector system 16 includes the set of data points $P_f(\beta, \gamma)$ generated by all the detectors at detector angles from $-\gamma_m+\alpha$ to $-\gamma_m$.

Such asymmetric detector systems are often used in CT scanners so as to increase the field of view (FOV) of the scanner without significantly increasing the cost of the detector system and associated DAS. The FOV of a scanner is determined by the angular extent of the detector system. For example, the FOV of a scanner using the symmetric detector system illustrated in FIG. 4 is equal to $2\gamma_m$, and the FOV of a scanner using the asymmetric detector system illustrated in FIG. 5 is equal to $2-\gamma_{m-}\alpha$. This suggests that the FOV provided by an asymmetric detector system is smaller than the FOV ($2\gamma_m$) provided by a comparable symmetric detector system. However, alternative symmetric and asymmetric detector systems are properly compared by considering the angular extent of the symmetric portion of the asymmetric detector system to be equal or nearly equal to the angular extent of the alternative symmetric detector system, i.e., the $-\gamma_{m-}\alpha$ portion of the asymmetric detector system is equal or nearly equal to $\gamma_m$ of the alternative symmetric detector system. So use of the asymmetric detector system effectively increases the FOV of the scanner by $\alpha$.

Another advantage of asymmetric detector systems relates to the contribution that each individual detector makes to a tomogram. As is well known, the importance of each detector in terms of its contribution to tomograms decreases with increasing detector angle. So it is reasonable to eliminate half the detectors having a detector angle the absolute value of which is greater than a predetermined threshold.

Accordingly, the detector array 16 can be symmetrical or asymmetrical and any corresponding known CT "halfscan" technique can be employed with the imaging system 10 to create an image slice from each row of the detector array. Such scans require a rotation of the source and detectors around the X-axis of 180° plus the fan angle in order to acquire a complete set of data for reconstructing an image.

The number of projections required is dependent on the size of the detector array and the distance from the mechanical center of rotation of the machine. For example, using a 10 cm×10 cm detector array, and positioning the source 14 and array 16 each 50 cm from the center of rotation (so that the focal spot is 100 cm from the detector array), results in a value of $\gamma_m$ (calculated for a symmetric detector system) as follows:

$\gamma_m=\tan(0.05)=2.86°$

Thus, the entire detector array subtends an angle of 5.72°. A half scan reconstruction would therefore require rotation of the source and detector array of 185.72° to complete a scan. The value of each incremental projection angle is 5.72° thus requiring 33 projections to acquire enough data to provide a complete half scan reconstruction. If for any reason a complete 180° plus fan angle rotation cannot be completed, as for example, where the patient 30 and table 32 interfere with the completion of the 185.72° rotation, the scan can be made as closely as possible to approximate the 180° plus fan angle rotation, i.e., the 185.72° rotation in the example given (for example, an approx. 171.6° scan rotation using 30 projections each 5.72° apart can be used). Error correction data can then be generated to complete the scan. Thus, the present invention is not limited to a scan rotation of 180° plus fan angle, and where half scan techniques are used the 180° plus fan angle can be approximated.

Figure 8:
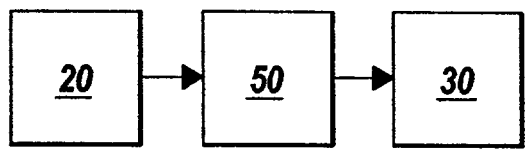
FIG. 8 illustrates a generalized block diagram showing basic elements of a mechanical system for partially rotating the patient table, or pallet.
Figure 7:
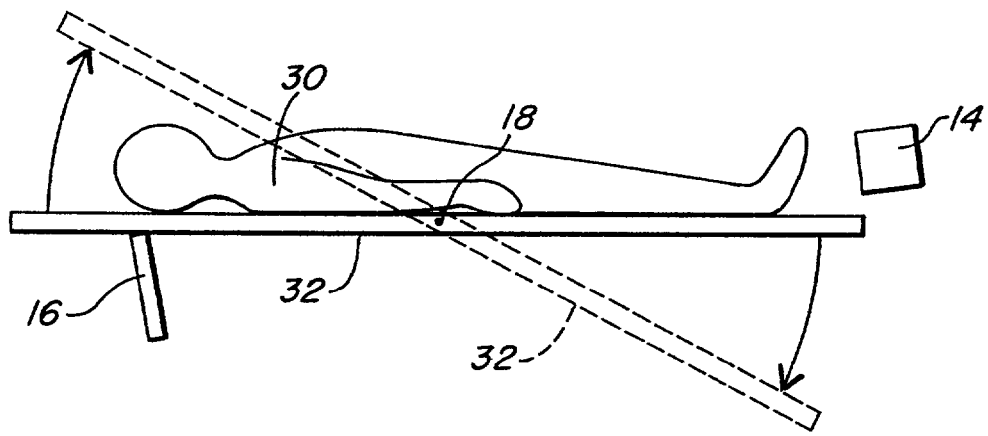
FIG. 7 illustrates a top view of the scanning system of FIG. 6.

Alternatively, as shown in FIG. 7, the table 30 can be rotated about the axis 18 relative to the source 14 and detector array 16 to make up the deficiency. In the example given above the relative rotation would make up the additional, roughly 14°. In such as case, the drive mechanism 20 is suitably coupled to the table 30 through a linkage mechanism 50 as shown in FIG. 8. In this case the table can be incremented approximately 14°/33 or 0.42°, with each 6.14° rotation of the support 12 to provide a relative rotation of 5.72°. The number of projections can then be increased to 33, with the table rotating approximately 14° (and the source and detector array rotating approximately 202.62° for a complete half-scan rotation) during a scan.

With a spacing of 50 cm between the source and the mechanical center and between the mechanical center and detector array provides a magnification of about 1.7. With detectors on the order of 85 microns square, this provides resolution on the order of $\frac{1}{10}^{th}$ the resolution currently available with conventional CT scanners.

With advances in molecular imaging, it is conceivable that materials, such as gold, and agents, such as exogenous contrast agents, can be used for in vivo imaging of cancer cells found the prostate using a scanner designed and constructed in accordance with the present invention. The scanner thus lends itself to in vivo imaging using such materials and agents so as to be visible in an X-ray image generated by the scanner.

Thus, using the CT scanner of this invention, contrast agents can provide for the immunoguided imaging of prostate with histopathological correlation, when used according to the methods known to those of skill in the radioimaging art. See, for example, J. W. Moul et al., "The role of imaging studies and molecular markers for selecting candidates for radical prostatectomy." Int J Radiat Oncol Biol Phys 49(5): 1281-6 (2001). Included among the exogenous contrast agents that can be used for in vivo imaging are molecular probes that bind with prostate or prostate carcinoma-specific markers. A. R. Bradwell et al., "Developments in Antibody Imaging", Monoclonal Antibodies for Cancer Detection and Therapy, R. W. Baldwin et al., (eds.), pp. 65-85 (Academic Press 1985), which is hereby incorporated by reference. Molecular probes that bind with prostate or prostate carcinoma-specific markers can be conjugated to atoms of gold, tungsten or other dense "high Z" elements, thus providing greater contrast for enhanced computed tomographic (CT) imaging by the CT scanner of the invention. For example, a prostate specific antibody can be conjugated to colloidal gold according to standard method of G. Frens, Nature, Phys. Sci. 241:20-22 (1973) or by improved methods known to those of skill in the immunological art. See, Catalog (Structure Probe, Inc., West Chester, Pa., USA); see also Research Diagnostics, Inc., Pleasant Hill Road, Flanders, N.J., USA. Anti-Prostate Specific Antigen (PSA) antibodies are known to specifically bind to prostate cancer cells. Sinha A A, et al., "Intravenous injection of an immunoconjugate (anti-PSA-IgG conjugated to 5-fluoro-2'-deoxyuridine) selectively inhibits cell proliferation and induces cell death in human prostate cancer cell tumors grown in nude mice." Anticancer Res. 19(2A):893-902 (1999). Anti-PSA antibody gold conjugates are known in the medical art (U.S. Pat. No. 6,017,703) and have been used commercially in in vitro diagnostic applications (PSA RapidScreen Test, Craig Medical Distribution, Vista, Calif. USA).

Alternatively, high Z element-conjugated molecular probes that bind to p27, p53, bcl-2, Ki-67 (MIB-1) or other prostate or prostate carcinoma-specific markers can be used. J. W. Moul et al., "The role of imaging studies and molecular markers for selecting candidates for radical prost,atectomy." Urol Clin North Am 28(3):459-72 (2001). Antibodies to prostatic acid phosphatase ("PAP") have been used to specifically bind prostate carconoma cells. See, U.S. Patent No. 6,019,957, incorporated in its entirety by reference. Antibodies to Prostate Membrane Specific Antigen (PMSA; Folic Acid Hydrolase) have also been used to identify cells of interest to this invention (Horoszewicz et al., Anticancer Res., 7:927-936, 1987; Carter et al., Proc. Nat'l Acad. Sci. USA 93: 749-753 (1996); Murphy et al., Cancer, 78: 809-818 (1996)), as have molecular probes for prostatic acid phosphatase (PAP) (Partin and Oesterling, J. Urol., 152:1358-1368 (1994)); prostate secreted protein (PSP) (Huang et al., Prostate, 23: 201-212 (1993)); human kallekrein 2 (HK2) (Piiuronen et al., Clin. Chem. 42: 1034-1041 (1996)); and the markers identified in U.S. Pat. No. 6,171,796 (An, et al.) and U.S. Pat. No. 6,090,559 (Russell, et al.). Anti-cathespin B gold-onjugated antibodies to (A. A. Sinha et al., "Plasma membrane association of cathepsin B in human prostate cancer: biochemical and immunogold electron microscopic analysis." Prostate. 49(3):172-84 (2001).) or conjugated molecular probes for the assessment of neovascularity (Weissleder, et al., "Molecular Imaging", Radiology, 219(2): 316-333 (2001)) can also be used.

Moreover, subtraction methodologies can provide improved contrast. A. R. Bradwell et al., "Developments in Antibody Imaging", Monoclonal Antibodies for Cancer Detection and Therapy, R. W. Baldwin et al., (eds.), pp. 65-85 (Academic Press 1985). Guidance for the use of subtraction methodologies in the screening for prostate cancer is provided by S. Kirac et al., "Detection of metastatic bone lesions in patients with prostate carcinoma: $^{99}$Tcm-monoclonal antibody imaging." Nucl. Med. Commun. 18(10):968-73 (1997).

Additional guidance for the construction and use of prostate and prostate carcinoma-specific molecular probes is provided by the use of capromab pendetide. $^{111}$Indium-conjugated capromab pendetide, for example, as available under the trade name PROSTASCINT® (Cytogen Corp., Princeton, N.J., USA), is a monoclonal antibody that is approved for use as an immunoscintigraphy diagnostic imaging agent in newly diagnosed patients with biopsy-proven prostate cancer. Capromab pendetide is thought to be clinically localized after standard diagnostic evaluation, who are at high risk for pelvic lymph node metastases, and in post-prostatectomy patients with a rising PSA and a negative or equivocal standard metastatic evaluation in whom there is a high clinical suspicion of occult metastatic disease. Kahn et al., "111-Indium Capromab Pendetide in the Evaluation of Patients with Residual or Recurrent Prostate Cancer after Radical Prostatectomy," J. Urol. 159(6):2041-6 (1998); Lamb et al., "Capromab Pendetide: A Review of Its Use as an Imaging Agent in Prostate Cancer," Drugs Aging 12(4):293-304 (1998); Kahn et al., "Radioimmunoscintigraphy with In-111-labeled Capromab Pendetide Predicts Prostate Cancer Response to Salvage Radiotherapy after Failed Radical Prostatectomy," Journal of Clinical Oncology, 16(1), 284-289 (January 1998). The capromab pendetide test produces a immunoscintigraphic image that can be used to detect lesions as small as 5 millimeters and has been shown in earlier studies to detect metastatic prostate disease in men with high PSA levels. In addition, the capromab pendetide immunoscintigraphic test has been used in evaluating men with mildly elevated PSA levels, often indicating early recurrence of cancer. G. V. Raj et al., "Clinical utility of indium $^{111}$-capromab pendetide immunoscintigraphy in the detection of early, recurrent prostate carcinoma after radical prostatectomy." Cancer 94(4):987-96 (2002). A technique has been developed that superimposes a immunoscintigraphic image from a PROSTASCINT® scan with a conventional pelvic CT image (in which the image slices are taken through the pelvic bones) for the purpose of designing brachytherapy that targets areas at high risk for treatment failure. R. J. Ellis et al., "Radioimmunoguided imaging of prostate cancer foci with histopathological correlation." Int. J. Radiat. Oncol. Biol. Phys. 49(5):1281-6 (2001).

For use with the CT scanner of the invention, a useful capromab pendetide agent can be produced by substituting gold, tungsten or other dense "high Z" elements for the conjugated $^{111}$indium of PROSCTASCINT®, thus providing a contrast agent for enhanced computed tomography (CT) rather than immunoscintigraphy. For guidance in the labeling and use of prostate specific antibodies and peptides, see U.S. Pat. Nos. 5,162,504 5,763,202, 6,015,561 and 6,150,508, incorporated in their entirety by reference.

The invention may be embodied in other specific forms without departing from the spirit or central characteristics thereof. The present embodiments are, therefore, to be considered in all respects as illustrative and not restrictive, the scope of the invention being indicated by appending claims rather than by the foregoing description, and all changes that come within the meaning and range of equivalency of the claims are therefore intended to be embraced therein.

What is claimed is:

1. A method of in vivo imaging of a portion of the lower abdomen of a patient, comprising:
   rotating a X-ray source and detector about a rotation axis that extends substantially perpendicular to the sagittal plane of the patient, wherein X-ray emission from the X-ray source pass between the pelvic bones of the patient, wherein the source and detector are configured so as to define a fan beam and fan beam angle, and the detector array is controlled to rotate a minimum of approximately 180° plus an angle equal to the fan beam angle during a scan;
   detecting radiation that has traversed the patient injected with a material including a high contrast material for X-ray imaging and a material for binding the high contrast material to a specific biological site if present in the portion of the lower abdomen of the patient; and
   generating a CT image of the portion of the lower abdomen of the patient so as to generate an image of the portion of the lower abdomen of the patient, wherein a scanning plane of the CT image extends between and excludes the pelvic bones of the patient so as to exclude relatively dense bone from the scanning plane while including relatively soft tissue therebetween.

2. A method according to claim 1, wherein the high contrast material is a dense high Z element.

3. A method according to claim 2, further including injecting the patient with a material including a high contrast material for X-ray imaging and a material for binding the high contrast material to a specific biological site if present in the portion of the lower abdomen of the patient, wherein the high contrast material is a metal selected from the group consisting of gold and tungsten.

4. A method according to claim 1, further including injecting the patient with a material including a high contrast material for X-ray imaging and a material for binding the high contrast material to a specific biological site if present in the portion of the lower abdomen of the patient,; and wherein the material for binding the high contrast material to a specific biological site includes a molecular probe that binds with prostate or prostate carcinoma-specific markers.

5. A method according to claim 1, further including injecting the patient with a material including a high contrast material for X-ray imaging and a material for binding the high contrast material to a specific biological site if present in the portion of the lower abdomen of the patient, wherein the material for binding the high contrast material to a specific biological site includes a monoclonal antibody.

6. A method according to claim 1, wherein generating a CT image of the portion of the lower abdomen includes generating a non-pelvic CT scanned image.

7. A method according to claim 1, wherein generating a CT image includes using a detector array comprising a plurality of detectors, each having a maximum width dimension of 150 microns and a maximum length dimension of 150 microns.

8. A method according to claim 7, wherein the high contrast material is a dense high Z element.

9. A method according to claim 8, further including injecting the patient with a material including a high contrast material for X-ray imaging and a material for binding the high contrast material to a specific biological site if present in the portion of the lower abdomen of the patient, wherein the high contrast material is a metal selected from the group consisting of gold and tungsten.

10. A method according to claim 7, further including injecting the patient with a material including a high contrast material for X-ray imaging and a material for binding the high contrast material to a specific biological site if present in the portion of the lower abdomen of the patient, wherein the material for binding the high contrast material to a specific biological site includes a molecular probe that binds with prostate or prostate carcinoma-specific markers.

11. A method according to claim 7, further including injecting the patient with a material including a high contrast material for X-ray imaging and a material for binding the high contrast material to a specific biological site if present in the portion of the lower abdomen of the patient, wherein the material for binding the high contrast material to a specific biological site includes a monoclonal antibody.

12. A method according to claim 7, wherein the detectors are square.

13. A method according to claim 12, wherein the detectors are about 85 microns in length on a side.

14. A method according to claim 1, wherein the scanning plane is defined by a rotation axis oriented so as to extend substantially perpendicular to the height of the patient.

15. A CT scanner for in vivo imaging of a patient injected with a material including a high contrast material for X-ray imaging and a material for binding the high contrast material to a specific biological site if present in a portion of the lower abdomen of the patient, the scanner comprising:
an X-ray source;
a detector array including at least one row of detectors;
a source and detector array support configured so as to rotate the source and detector array about a rotation axis configured and arranged substantially perpendicular to the sagittal plane of the patient, wherein X-ray emission from the X-ray source pass between the pelvic bones of the patient; so as to define at least one scanning plane for acquiring data for a CT image, wherein the source and detector are configured so as to define a fan beam and fan beam angle, and the detector array is controlled to rotate a minimum of approximately 180° plus an angle equal to the fan beam angle during a scan; and
a patient support configured so as to support the patient in a specific orientation so that the scanning plane does not include the pelvic bones of the patient positioned on the patient support so as to exclude relatively dense bone from the scanning plane while including relatively soft tissue therebetween.

16. A CT scanner according to claim 15, wherein the high contrast material is a dense high Z element.

17. A CT scanner according to claim 16, wherein the high contrast material is a metal selected from the group consisting of gold and tungsten.

18. A CT scanner according to claim 15, wherein the material for binding the high contrast material to a specific biological site includes a molecular probe that binds with prostate or prostate carcinoma-specific markers.

19. A CT scanner according to claim 15, wherein the material for binding the high contrast material to a specific biological site includes a monoclonal antibody.

20. A CT scanner according to claim 15, wherein the source and detector array support rotates through an angle sufficient to acquire sufficient data for half scan reconstruction.

21. A CT scanner according to claim 15, wherein the source and detector are configured so as to define a fan beam and fan beam angle, and the detector array rotates a minimum of approximately 180° plus an angle equal to the fan beam angle during a scan.

22. A CT scanner according to claim 15, wherein the patient support remains fixed as the source and detector array support rotates through a predetermined angle.

23. A CT scanner according to claim 15, wherein the patient support rotates from a preselected angle as the source and detector array support rotate through a predetermined angle.

24. A CT scanner according to claim 15, wherein the detector array is asymmetrical.

25. A CT scanner according to claim 15, wherein the detector array is symmetrical.

26. A CT scanner according to claim 15, wherein the scanner is configured so as to perform a constant z-axis position scan.

27. A CT scanner according to claim 15, wherein
the detector array comprises a plurality of detectors, each having a maximum width dimension of 150 microns and a maximum length dimension of 150 microns.

28. A CT scanner according to claim 27, wherein the high contrast material is a dense high Z element.

29. A CT scanner according to claim 28, wherein the high contrast material is a metal selected from the group consisting of gold and tungsten.

30. A CT scanner according to claim 27, wherein the material for binding the high contrast material to a specific biological site includes a molecular probe that binds with prostate or prostate carcinoma-specific markers.

31. A CT scanner according to claim 27, wherein the material for binding the high contrast material to a specific biological site includes a monoclonal antibody.

32. A CT scanner according to claim 27, wherein the detectors are square.

33. A CT scanner according to claim 32, where each detector has a dimension on the order of 85 square microns.

34. A CT scanner according to claim 27, wherein the detectors are rectangular.

35. A CT scanner according to claim 15, wherein the rotation axis is oriented so as to extend substantially perpendicular to the height of the patient.

36. A method of scanning a portion of the lower abdomen of a patient using computed tomography techniques comprising:

rotating a X-ray source and detector about a rotation axis that extends substantially perpendicular to the sagittal plane of the patient, wherein X-ray emission from the X-ray source pass between the pelvic bones of the patient, wherein the source and detector are arranged so as to define a fan beam and fan beam angle, and including rotating the detector array a minimum of approximately 180° plus an angle equal to the fan beam angle during a scan;

positioning the patient within a CT scanner so that one or more scanning planes created by the rotation of the X-ray source and detector array of the scanner is provided between the pelvic bones of the patient so as to exclude relatively dense bone from the one or more scanning planes while including relatively soft tissue therebetween.

37. A method according to claim 36, further including injecting the patient with a material including a high contrast material for X-ray imaging and a material for binding the high contrast material to a specific biological site if present in the portion of the lower abdomen of the patient, wherein the high contrast material is a dense high Z element.

38. A method according to claim 36, further including injecting the patient with a material including a high contrast material for X-ray imaging and a material for binding the high contrast material to a specific biological site if present in the portion of the lower abdomen of the patient, wherein the high contrast material is a metal selected from the group consisting of gold and tungsten.

39. A method according to claim 36, further including injecting the patient with a material including a high contrast material for X-ray imaging and a material for binding the high contrast material to a specific biological site if present in the portion of the lower abdomen of the patient, wherein the material for binding the high contrast material to a specific biological site includes a molecular probe that binds with prostate or prostate carcinoma-specific markers.

40. A method according to claim 36, further including injecting the patient with a material including a high contrast material for X-ray imaging and a material for binding the high contrast material to a specific biological site if present in the portion of the lower abdomen of the patient, wherein the material for binding the high contrast material to a specific biological site includes a monoclonal antibody.

41. A method according to claim 36, further comprising rotating the source and detector array through a predetermined angle sufficient to acquire sufficient data for half scan reconstruction.

42. A method according to claim 36, comprising fixing the patient as the source and detector array rotate through a predetermined angle.

43. A method according to claim 36, comprising: rotating the patient support through a preselected angle as the source and detector array support rotate through a predetermined angle.

44. A method according to claim 36, comprising using a asymmetrical detector array.

45. A method according to claim 36, comprising using a symmetrical detector array.

46. A method according to claim 36, comprising performing a constant z-axis position scan.

47. A method according to claim 36, comprising:

using a detector array comprising a plurality of detectors, each having a maximum width dimension of 150 microns and a maximum length dimension of 150 microns so as to increase the resolution of an image generated from data acquired by the scanner.

48. A method according to claim 47, comprising using a detector array comprising a plurality of square detectors.

49. A method according to claim 47, comprising using a detector array comprising detectors, each on the order of 85 square microns.

50. A method according to claim 47, comprising using a detector array comprising a plurality of rectangular detectors.

* * * * *

UNITED STATES PATENT AND TRADEMARK OFFICE
CERTIFICATE OF CORRECTION

PATENT NO.        : 7,664,543 B2                                                Page 1 of 1
APPLICATION NO. : 10/133054
DATED             : February 16, 2010
INVENTOR(S)       : Bernard M. Gordon It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1792 days.

Signed and Sealed this

Thirtieth Day of November, 2010

David J. Kappos
*Director of the United States Patent and Trademark Office*